(12) United States Patent
Lin et al.

(10) Patent No.: US 10,359,350 B1
(45) Date of Patent: Jul. 23, 2019

(54) METHOD AND SYSTEM FOR PARTICLE CHARACTERIZATION IN HARSH ENVIRONMENTS

(71) Applicants: Hai Lin, Rancho Cucamonga, CA (US); Gregor Arthur Waldherr, Rancho Cucamonga, CA (US)

(72) Inventors: Hai Lin, Rancho Cucamonga, CA (US); Gregor Arthur Waldherr, Rancho Cucamonga, CA (US)

( * ) Notice: Subject to any disclaimer, the term of this patent is extended or adjusted under 35 U.S.C. 154(b) by 0 days.

(21) Appl. No.: 15/878,117

(22) Filed: Jan. 23, 2018

(51) Int. Cl.
*G01N 21/00* (2006.01)
*G01N 15/02* (2006.01)
*G01N 15/00* (2006.01)
*G01N 15/14* (2006.01)
*G01N 21/53* (2006.01)

(52) U.S. Cl.
CPC ..... *G01N 15/0211* (2013.01); *G01N 15/1456* (2013.01); *G01N 21/532* (2013.01); *G01N 2015/0049* (2013.01); *G01N 2015/0096* (2013.01); *G01N 2015/0238* (2013.01); *G01N 2015/1493* (2013.01)

(58) Field of Classification Search
CPC .......... G01N 15/0205; G01N 15/0211; G01N 15/1012; G01N 15/1404; G01N 15/1459; G01N 2015/0003; G01N 2015/0046; G01N 2015/1075; G01N 2015/1493; G01N 2015/1497; G01N 2015/025; G01N 21/255; G01N 21/31; G01N 21/1702; G01N 21/47; G01N 21/53; E21B 47/10; E21B 47/101; E21B 49/10; E21B 49/08
See application file for complete search history.

(56) References Cited

U.S. PATENT DOCUMENTS

| | | | | |
|---|---|---|---|---|
| 4,798,465 | A * | 1/1989 | Knollenberg | G01N 15/0205 356/336 |
| 4,953,978 | A * | 9/1990 | Bott | G01N 15/0211 356/336 |
| 5,610,712 | A * | 3/1997 | Schmitz | G01N 15/0211 356/335 |
| 5,731,875 | A * | 3/1998 | Chandler | G01N 15/0205 356/336 |
| 6,311,471 | B1 * | 11/2001 | Waldherr | F02C 3/30 60/39.55 |
| 6,321,608 | B1 * | 11/2001 | Wagner | B82Y 15/00 73/863.21 |
| 6,490,040 | B1 * | 12/2002 | Berthold | G01N 21/53 356/342 |
| 7,518,719 | B2 * | 4/2009 | Sprenger | G01N 15/06 356/243.2 |
| 9,714,967 | B1 * | 7/2017 | Weickert | G01N 27/61 |
| 2009/0039249 | A1 * | 2/2009 | Wang | G01N 15/0205 250/287 |

(Continued)

*Primary Examiner* — Sang H Nguyen

(57) ABSTRACT

Disclosed herein is a novel optical particle characterization system and method of use that can be applied to harsh environments. By separating the sensing components from the electronics unit and using optical fibers for interconnection, only the sensing components need to endure harsh environmental conditions. This reduces the design constraints on the electronics unit and permits the incorporation of optical components into the sensing probe that can withstand high-temperature and high-pressure environments.

20 Claims, 3 Drawing Sheets

(56) References Cited

U.S. PATENT DOCUMENTS

| | | | | |
|---|---|---|---|---|
| 2010/0288921 A1* | 11/2010 | Wang | ................. | G01N 15/0205 250/287 |
| 2013/0085199 A1* | 4/2013 | Tamori | ............... | B01D 15/3804 521/149 |
| 2016/0313233 A1* | 10/2016 | Zangmeister | ...... | G01N 21/1702 |

* cited by examiner

METHOD AND SYSTEM FOR PARTICLE CHARACTERIZATION IN HARSH ENVIRONMENTS

GOVERNMENT RIGHTS

The invention described herein was made under a contract from U.S. Navy NAVAIR contract number N68335-12-C-0040. The government may have rights under this invention.

REFERENCES CITED

U.S. Patent Documents

| Document Number | Date | Name | US Classification |
|---|---|---|---|
| US-2010/0288921 A1* | November 2010 | Wang et al. | 250/287 |
| US-2009/0039249 A1* | February 2009 | Wang et al. | 250/287 |
| US-9,714,967 B1 | July 2017 | Weickert et al. | 324/456 |
| US-7,518,719 B2 | April 2009 | Sprenger et al | 356/243.2 |
| US-6,490,040 B1* | December 2002 | Berthold | 356/342 |
| US-6,321,608 B1* | November 2001 | Wagner et al. | 73/863.21 |
| US-5,731,875 A | March 1998 | Chandler | 356/336 |
| US-5,610,712 A | March 1997 | Schmitz | 356/335 |
| US-4,953,978 A | September 1990 | Bott et al. | 356/336 |
| US-4,798,465 A | January 1989 | Knollenberg | 356/336 |

*cited by examiner

TECHNICAL FIELD

The present subject matter relates generally to particle, dust, and debris sensors, and more particularly, to optical sensors which detect particles, dust, and/or debris within extreme temperature, pressure or severe electro-magnetic interference (EMI) environments such as engines, including but not limited to gas turbine engines, power generation engines, industrial engines, land-based engines, marine engines, or similar harsh environment. The system can also apply to both air and liquid media.

BACKGROUND ART

This invention addresses the need to characterize particles within harsh environments. It was initially inspired by the need to quantify particle ingestion by an aircraft gas turbine engine employed in an aircraft. Such aircraft are increasingly being called upon to operate in harsh environments, particularly those with a significant presence of sand and dust. Ingestion of sand and dust by a gas turbine engine can result in erosion of hardware, clogging of passageways, and deterioration of cooling systems. This leads to degradation of the engine's performance and ultimately could lead to engine failure. Engine manufacturers and customers would prefer to implement real-time health monitoring to detect airborne sand/dust and its penetration into the core of the engine where the most substantial damage can occur. Available particle measurement systems are not rugged enough to be applied to the harsh environment encountered within a gas turbine engine. Such a harsh environment may have extreme temperatures ranging from −100° F. (−73° C.) to 570° F. (300° C.) or more and pressure ranging from 0 psia (0 MPa) to 250 psia (1.7 MPa) or more. A traditional particle measurement system, for example, an optical particle sensor with integrated laser source and detector electronics, would likely not survive or function properly under such extreme conditions. Also, as the government imposes ever more stringent regulations regarding the emission of particulate matter (PM) by engines, the monitoring of those emissions becomes paramount.

The use of optical scattering methods for particle characterization has been repeatedly demonstrated for applications such as contamination monitoring in clean facilities, pharmaceutical and food preparation, indication of indoor air quality, and the monitoring of environmental pollution caused by industrial and vehicular emissions, biomass burning, volcanic activity, and dust upheaval by wind and vehicles. These methods are applied in relatively benign environments where temperature and pressure do not differ significantly from atmospheric conditions. Particle measurement systems employing these methods typically integrate the sensing probe components and electronic processing and control components into one unit. As such, the more delicate components of the particle measurement system cannot generally survive in harsh environments. Also, most particle measurement systems use electrical signals and near a harsh environment these signals are prone to electromagnetic interference (EMI) effects.

Accordingly, the present disclosure is directed to a novel sensing methodology that addresses the aforementioned deficits. More specifically, the present disclosure is directed to a particle measurement system that includes one or more sensor probes interconnected via optical fibers or cables to one or more isolated electronic units to detect dust particles and/or debris within an engine such as a gas turbine engine. By splitting passive optical components from temperature (and condition) sensitive components, such as the laser(s) and electronics within the electronics unit, only the sensor probe components are exposed to the harsh environment. Also, since optical fibers are used to interconnect the sensor probe and electronics unit the system is also more resistant to EMI effects. To survive the harsh environment the sensor probe is typically a sealed unit and, as such, can be used in both gaseous and liquid environments.

SUMMARY OF INVENTION

In general, the disclosed invention relates to, but is not limited to, the measurement of size, size distribution, and mass concentrations of particles in harsh environments. Specifically, this disclosure relates to the design and construction of an apparatus that uses light scattering or light obscuration for making such measurements. This apparatus has sensing components connected by optical fiber to electronics which allows the electronic components to be remotely located and isolated from a harsh environment. Together, the sensing components within the sensor probe(s), the optical fiber(s) and/or cable(s), and the electronics within the electronic unit(s) comprise the novel particle measurement system outlined in this disclosure.

The sensor probe(s) of the particle measurement system contain the optical components necessary to manipulate the transmitted and received light to and from a detection zone. Light transmitted into the sensor probe from the interconnecting optical fiber(s) is guided towards the detection zone by appropriate optical components known to those skilled in the art. Light scattered from the detection zone is received by those same or separate optical components and transmitted out of the sensor probe by the same or separate optical fiber(s). As such, only optical components are needed within the sensor probe, allowing the sensor probe to withstand the extremes of a harsh environment. All of the components of the sensor probe may be designed to survive low or high temperatures, low or high pressures, and EMI by appropriate choice of materials. There are many housing materials and optical materials, known to those skilled in the art, that can survive various pressure and temperature extremes. For example, a sensor probe with a stainless-steel housing, silica optical fibers, and optical elements made of silica and/or sapphire can withstand temperatures ranging from cryogenic to 1000° F. (538° C.). Since the signals within the sensor probe are optical, the sensor probe is inherently resistant to EMI. The various components of the sensing probe can be fixed together by various methods, known to those skilled in the art, including fusion, adhesives (epoxies, cements, etc.), and mechanical attachment (clamps, set screws, etc.). The method used to fix the components together may impose additional limits on the allowable pressure and temperature range. For example, fixing the components together using an epoxy with an upper useful temperature limit of 250° F. (121° C.) would impose that temperature limit upon the sensing probe itself.

The interconnecting optical fibers and/or cables transmit light between the sensor probe(s) and one or more electronics units. These fibers may include connectors on either end or both ends of the fibers. When multiple fibers are incorporated into a single cable the cable ends may similarly include multiple or single connectors on either end or both ends of the cable. When connectors are not included on fiber or cable ends, the individual fibers are separately secured within the sensor probe(s) or electronics unit(s) to guide the light appropriately.

The electronics unit(s) contain the light source(s), optical detector(s), and additional optical and electronic components to provide light to the sensor probe(s) and receive light collected from those same probe(s). Each light source, such as a laser, is coupled into an optical fiber using methods known to those skilled in the art. An optical fiber is then connected to either the exterior of the electronics unit or directly to the sensor probe. Additionally, an optical fiber containing a light source may be connected to a fiber coupler to allow two-way transmission of light to and from the sensor probe. Each optical detector may also be coupled into an optical fiber using methods known to those skilled in the art. That optical fiber could then be connected to either the exterior of the electronics unit or directly to the sensor probe. Additionally, an optical fiber coupled to a detector may be connected to a fiber coupler to allow two-way transmission of light to and from the sensor probe. The electronic components are used to drive the light sources(s), condition the output of the detector(s), and may incorporate additional signal processing capabilities into the electronics unit.

It is also possible to use multiple light sources with different wavelengths to realize wavelength-dependent responses. When multiple light sources with different wavelengths are used, the light from an individual optical fiber with a return signal could be sent through wavelength dispersion or wavelength selection elements using methods known to those skilled in the art. This is useful in cases were a wavelength-dependent scattering response can be expected.

Using a light source for illumination, a particle passing through the sensing location scatters light in all directions. An optical detector aimed at the sensing location from any orientation responds to a passing particle by generating a pulse signal whose amplitude may depend on particle diameter, particle shape, and particle composition. For certain detector orientations and arrangements, the amplitude of the pulse signal can be related monotonically to the particle diameter. For such orientations, as pulses are continually received over time, a histogram of particle diameters can be generated to provide a particle size distribution and additional particle statistics including average particle size. Counting the total number of particles passing within a finite time can provide particle load rate (also known as total number concentration and similar). Given a particle distribution over a finite measurement time, in combination with known mass density of the particles, the mass concentration can be determined. Thus, using signal processing, the passage of multiple particles can generate many particle statistics including particle size distributions, particle load rates, and mass concentration. This type of signal processing is known to those skilled in the art and can be performed in hardware or software.

DESCRIPTION OF EMBODIMENT

The above, as well as other objects and advantages of this disclosure, will become readily apparent to those skilled in the art from reading the following description of an embodiment of the invention. The description and drawings illustrate exemplary embodiments of the invention and serve to enable one skilled in the art to make or use the invention and are not intended to limit the scope of the invention in any manner. With respect to the methods disclosed and illustrated, the steps presented are exemplary in nature, and thus, the order of the steps is not necessary or critical.

As used herein, the terms "first", "second", "third", and "fourth" may be used interchangeably to distinguish one component from another and are not intended to signify location or importance of the individual components.

The present disclosure uses an in-situ approach wherein a sensor probe separates the light source(s), detector(s), and electronics from the harsh measurement zone by using an interconnecting optical fiber cable. Some of the interconnecting optical fibers transmit the light source(s) to the detection zone and may also simultaneously transmit the measured scattered light back to the detectors through either a single cable connector or multiple connectors. The optical fiber configuration can range anywhere from multiple single-core fibers to one multi-core fiber to a single single-core fiber with multiplexed data to any combination thereof. Individual optical fibers can be either multi-mode optical fibers, single-mode optical fibers, or polarization-maintaining optical fibers, as determined by the requirements of the sensor system and the system may include any combination of these optical. If desired, the sensor probe could be mounted flush to the process wall and have a single connector. The sensor probe contains beam-shaping optics, collection optics, optical apertures, and optical fibers, all of which can be designed to survive high temperature environments, since no electronic components included in the sensing probe. For engine dust ingestion and other applications, multiple sensors could also be placed at multiple sensing locations to better grasp the spatial variation in particle characteristics.

Figure 1:
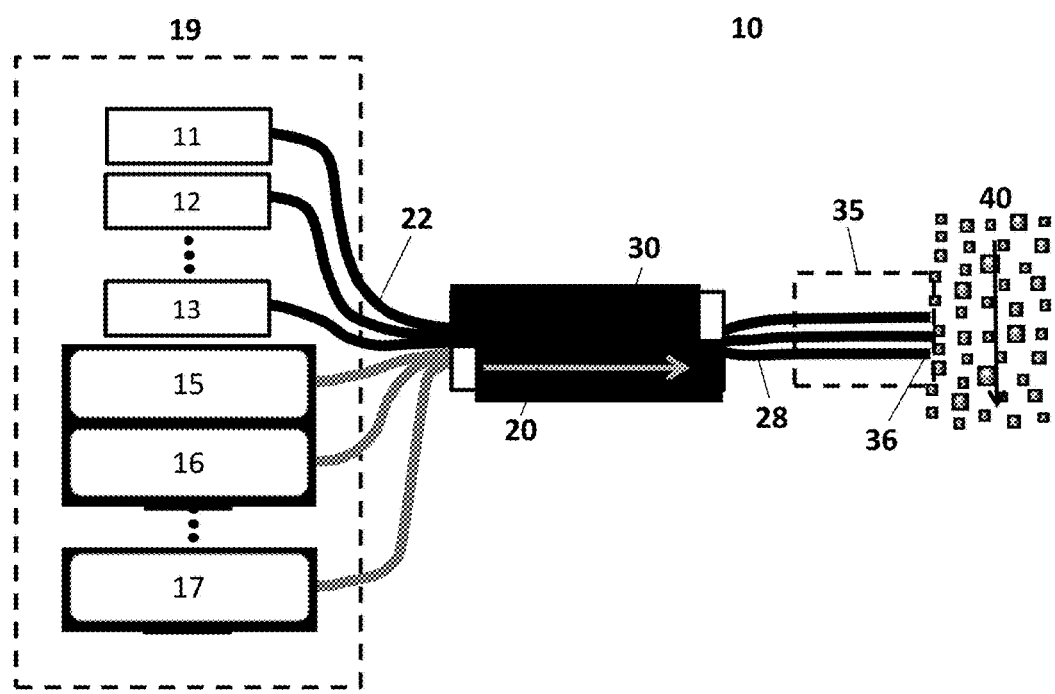
FIG. 1 shows the particle measurement system concept with sensor probe, electronics unit including light sources and detectors, and interconnecting optical fiber(s).

The fiber-based design is flexible and allows implementation of single or multiple light sources and single or multiple optical detectors. FIG. 1 illustrates in schematic form, a sensor system 10 for accomplishing the invention. More specifically, there is provided an electronics unit 19 connected via fiber coupler 25 to a sensor probe 35 to measure the particles in a particle-laden flow 40. An entire sensor system may also include one or more electronics units 19, one or more fiber couplers 25, one or more sensor probes 35, and may interrogate one or more particle-laden flows 40. The electronics unit 19 may include one detector 11 or multiple detectors 12 and one light source 15 or multiple light sources 16 along with any additional optical components necessary to control the light transmitted from the light sources and to control the light into the detectors. The sensor probe 35 may include sensing tips 36 and any additional optical components necessary to control the light transmitted to and from the particle-laden flow 40. The optical coupler 25 connecting the sensor probe 35 and electronics unit 19, connects fibers from the electronics unit 22 to fibers from the sensor probe 28. The fiber coupler 25 may include single or multiple pathways for both transmitted light 20 and received light 30. Interconnection with optical fibers provides the advantage of flexible sensor mounting and placement while only exposing the sensor probe to harsh environments with moderate or high temperature and pressure, such as found in a gas turbine engine. Furthermore, this design allows a 1×n (or even m×n) coupler to be used if more detectors, more locations, and/or more light sources are monitored. In addition to design requirements such as dust size and range, flow rate or particle velocity, and concentration limit mentioned above, typically, sensor calibration for dust size quantitation is also required.

Figure 2:
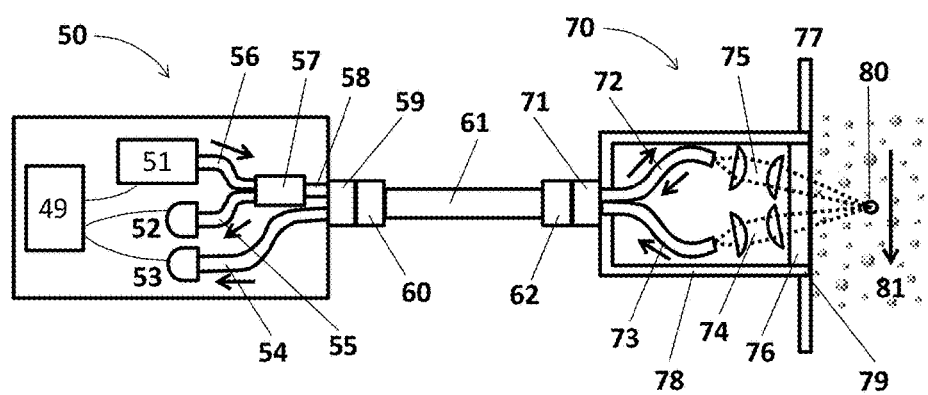
FIG. 2 illustrates an example of a specific engine-based implementation of the particle measurement system with one laser light source and two optical detectors.

FIG. 2 shows an example implementation of this invention with one light source and two detectors. More specifically, a sensor probe 70 is connected to an electronics unit 50 using an optical fiber bundle 61. A light source 51 transmits light through an optical fiber 56 to a fiber coupler 57. That fiber coupler transmits the light via optical fiber 58 to a first optical fiber connector 59 that is at the exterior of the electronics unit 50. Optical fiber connector 59 and all other optical fiber connectors in the system may consists of single or multiple fiber cores and may also consist of more than one connector. A second optical fiber connector 60 connects to fiber connector 59 and transmits the light source through an optical fiber core in the optical fiber bundle 61 to a third optical fiber connector 62. A fourth optical fiber connector 71, on the exterior of the sensor probe 70, connects to fiber connector 62 and transmits the light source into the sensor probe 70 via optical fiber 72. It should be noted that any pair of optical fiber connectors may be replaced by a continuous section of optical fiber, removing the ability to separate the optical path at that location. The light leaving optical fiber 72 may either be directly transmitted or may be reshaped using optical components 75, such as lenses. The transmitted light then passes through a window 76 to a sensing location 80 in the particle-laden flow 81. The spatial beam-shaping performed in 75 is done to achieve a defined performance at 80 and is known to those skilled in the art. In this illustration, the sensor probe 70 is mounted flush to the wall 77 confining the particle-laden flow 81. Whether the sensor probe is mounted flush is dependent on the application and is readily apparent to those skilled in the art. All elements of the sensor probe 70 are contained within an outer housing 78 with openings for the fiber connector 71 and window 76. The body of outer housing 78 may also have a predetermined shape, such as a threaded end 79, configured to secure the probe into existing locations in the measurement application.

Particles in the sensing location 80 send scattered light back the sensor probe 70. The first scattered light passes into optical fiber 72 either directly or by passing through optical components 75. Similarly, the second scattered light passes into optical fiber 73 either directly or by passing through optical components 74. The spatial beam-shaping performed in 75 and 74 also achieves a defined performance at 72 and 73 for collected light and is known to those skilled in the art. Light entering optical fiber 72 passes back through the optical fiber bundle 61 and enters optical fiber 58 using the same pathway as the transmitted light. In the fiber coupler 57 the received scattered light is separated from the transmitted light and sent into optical fiber 55 and on to detector 52. Any method, known to those skilled in the art, can be used to separate the transmitted and received light, for example polarization rotation. Light entering optical fiber 73 is directed sequentially to the fourth optical fiber connector 71, the third optical fiber connector 62, the optical fiber bundle 61, the second optical fiber connector 60, the first optical fiber connector 59, and into optical fiber 54 where it is passed on to detector 53. The components of the electronics unit 50 are controlled by a controller 49 which provides voltage control, current control, and signal control to light source 51, detector 52, and detector 53. The controller 49 may also include individual control elements or signal processing elements at each component.

It should be obvious to those skilled in the art, that many variations on FIG. 2 are possible. Additional light sources, detectors, fibers, and connectors, may be included in the sensor probe 70, the electronics unit 50, and the optical fiber bundle 61. Additional sensor probes 70, electronics units 50, and optical fiber bundles 61 may also be included in a complete particle measurement system, especially for measurements at multiple distributed locations. The location of one optical fiber with respect to another optical fiber within the sensor probe can also be flexible. For example, optical fiber 72 and optical components 75 could be adjacent to optical fiber 73 and optical components 74, to build a compact probe. Alternately, a prescribed distance could separate the optical fibers and components, to examine different aspects of the particle light scattering. Additionally, various elements can be combined to optimize part count and aid in assembly. For example, some optical elements in 75 could be combined with optical fiber 72 to make an optical fiber focuser or an optical fiber collimator. Additionally, window 76 may be combined with other optical elements in 75 or 74 to convert the window into a focusing lens or a beam spreader. A single sensor probe 70 may also have multiple sensing locations 80, which may require additional fibers 72 and/or 73 and additional beam-shaping optics 74 and/or 75. Pairs of optical fiber interconnections, such as 62 and 71, may also be replaced by continuous optical fibers, removing connectivity but improving signal transmission and/or possible connection contamination.

Figure 3:
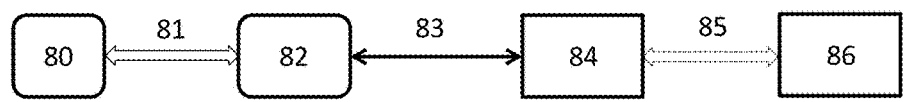
FIG. 3 illustrates a complete sensor system comprising sensor probe and sensor electronics interconnected with optical fiber(s), a signal processing unit, and a local or remote display and control.

FIG. 3 shows the sensor system connected to additional signal processing resources. The sensor probe 80, optical fiber 81, and electronics unit 82 have been described previously. The electronics unit 82 may then be connected by electrical wires and cable 83 to additional signal processing hardware 84. Processing hardware 84 may then interface with a local or remote display or control system 86 via communication lines 85. System 86 can be used to display the results from the processing hardware 84 or process the information further and may also be used to control the operation of the processing hardware 84.

An example of processing hardware 84 is a signal classifier. The signal classifier is an electronic device such as a FPGA- or DSP-based multichannel signal analyzer that classifies particles based on the pulse height of their scattering signal and is known to those skilled in the art. Based on the pulse amplitude of the detector signal created by a passing particle, the diameter of the particle can be classified. The classified diameters are then processed into particle characteristics such as particle size distribution, particle load rate (also known as total number concentration and similar), and particle mass concentration. For engine applications, the particle measurement system may be interfaced with an engine control unit to provide both engine health management and early warning of periods of excessive dust ingestion.

This written description uses examples to disclose the invention and also enables any person skilled in the art to practice the invention, including making and using any devices or systems and performing any incorporated methods. The claims define the patentable scope of the invention, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for optically detecting particles and measuring size distributions and mass concentrations of particulate matter in a gas or a liquid, the system comprising:
   one or more sensing probes each consisting of at least one or more light source pathways and at least one or more sensing pathways, where the source pathways direct a plurality of light beams through optional beam-shaping optics and into one or more detection zones and the sensing pathways have a plurality of optics that collects light scattered from particles in the detection zones and relays those optical signals to the electronics unit;
   one or more electronics units that houses a plurality of light sources, a plurality of detectors which convert the optical light scattering signal generated by particles passing through the detection zones into pulsed electrical signals whose amplitudes depend on the particle size, particle shape, and particle composition, corresponding light source and detector control electronics, a signal classifier which provides a plurality of size channels into which the measured pulsed signals are classified, and signal processing hardware to convert the classified pulsed signals into particle statistics including particle distribution, total particle volume, average particle size, average particle surface area, and particle mass concentration;
   and a plurality of optical fiber connections between the sensing probes and electronics units.

2. The particle measurement system described in claim 1 where only one sensing probe and one electronics unit are used.

3. The particle measurement system described in claim 1 where only one light source and/or one detector is included.

4. The particle measurement system described in claim 1 where the signal classifier is a multichannel pulse height discriminator or signal analyzer which provides a plurality of size channels numbering from 1 to 16,777,216 channels.

5. The particle measurement system described in claim 1 where the interconnecting optical fibers for one sensor probe are all contained within one optical fiber cable.

6. The particle measurement system described in claim 1 where one light source and one detector are coupled on two separate optical fibers or only one optical fiber with the use of a fiber coupler.

7. The particle measurement system described in claim 1 where only one light source and two or more detectors are included.

8. The particle measurement system described in claim 1 where light along the optical paths in the sensing probe is spatially beam shaped to achieve a defined performance at the sensing location.

9. The particle measurement system described in claim 1 where each optical path has its own set of optical elements to shape the beam.

10. The particle measurement system described in claim 1 where optical elements are shared on multiple optical paths.

11. The particle measurement system described in claim 1 where the sensing probe is capable of withstanding pressures between 0 psia (0 MPa) and 250 psia (1.7 MPa) or more.

12. The particle measurement system described in claim 1 where the sensing probe is capable of withstanding elevated temperatures as high as 570° F. (300° C.) or higher and reduced temperatures as low as −100° F. (−73° C.) or lower.

13. The particle measurement system described in claim 1 where the outer housing of a sensor probe comprises a predetermined shape, wherein this predetermined shape is generally cylindrical and may include one end threaded to secure the sensor probe to a mounting location.

14. The particle measurement system described in claim 1 deployed with multiple light sources which may have same or different emission wavelengths.

15. The particle measurement system described in claim 1 wherein the signals from two or more detectors are summed, differenced, or ratioed to provide noise cancellation or other signal processing and interpretation.

16. The particle measurement system described in claim 1 deployed multiply or in a distributed fashion where the system could share common light sources or multiple detectors.

17. A method for optically detecting particles and measuring size distributions and mass concentrations of particulate matter in a gas or a liquid, the method comprising:
   providing a sensing probe in one or more locations, wherein each sensor probe consists of at least one light source pathway and at least one sensing pathway, where the source pathway directs a plurality of light beams through optional beam-shaping optics and into one or more detection zones and the sensing pathway has a plurality of optics that collect light scattered from particles in the detection zones and relays those optical signals to the electronics unit;
   providing one or more electronics units in one or more locations, wherein each electronics unit houses a plurality of light sources, a plurality of detectors which convert the optical light scattering signal generated by particles passing through the detection zones into pulsed electrical signals whose amplitudes depend on the particle size, particle shape, and particle composition, corresponding light source and detector control electronics, a signal classifier which provides a plurality of size channels into which the measured pulsed signals are classified, and signal processing hardware to convert the classified pulsed signals into particle statistics including particle distribution, total particle volume, average particle size, average particle surface area, and particle mass concentration;

and providing a plurality of optical fiber connections between the sensing probes and electronics units.

18. The method of claim 17 applied to monitoring a gas turbine engine to provide early warning and protection from excessive particle ingestion.

19. The method of claim 17 applied to monitoring the effectiveness of a filtration system by measuring the particle concentration before and after filtration.

20. The method of claim 17 applied to liquid media for water, oil, or lubricant contamination monitoring.

* * * * *